(12) United States Patent
Pohl

(10) Patent No.: US 7,517,506 B2
(45) Date of Patent: *Apr. 14, 2009

(54) PROCESS FOR THE PRODUCTION OF ALKYLBENZENE WITH ETHANE STRIPPING

(75) Inventor: Stephen L. Pohl, Wayne, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 289 days.

This patent is subject to a terminal disclaimer.

(21) Appl. No.: 11/435,512

(22) Filed: May 17, 2006

(65) Prior Publication Data

US 2006/0204410 A1 Sep. 14, 2006

Related U.S. Application Data

(62) Division of application No. 10/457,863, filed on Jun. 10, 2003, now Pat. No. 7,071,369.

(51) Int. Cl.
*B01J 8/04* (2006.01)
*C07C 2/64* (2006.01)
*C07C 2/00* (2006.01)

(52) U.S. Cl. .................. 422/188; 585/310; 585/314; 585/315; 585/319; 585/323; 585/449

(58) Field of Classification Search .................. 422/188; 585/310, 314, 315, 316, 319, 323, 449
See application file for complete search history.

(56) References Cited

U.S. PATENT DOCUMENTS

| 3,200,164 A | 8/1965 | Gerald |
| 3,205,277 A | 9/1965 | Pollitzer et al. |
| 3,428,701 A | 2/1969 | Ward |
| 3,691,245 A | 9/1972 | Helzner |
| 3,843,739 A | 10/1974 | Harper et al. |
| 4,008,290 A | 2/1977 | Ward |
| 4,048,243 A | 9/1977 | Ruckelshauss |

(Continued)

FOREIGN PATENT DOCUMENTS

EP 0 733 608 1/2000

*Primary Examiner*—Walter D Griffin
*Assistant Examiner*—Huy-Tram Nguyen
(74) *Attorney, Agent, or Firm*—Dilworth & Barrese LLP

(57) ABSTRACT

A process for the production of alkylbenzene includes introducing benzene and an olefin feed into a first alkylation reaction zone in the presence of a first alkylation catalyst under first alkylation reaction conditions to produce a first alkylation effluent containing alkylbenzene and a first alkylation overhead stream. The first alkylation overhead stream is separated into a liquid portion containing benzene and a vapor portion containing unconverted olefin and ethane. A major portion of the unconverted olefin in the vapor portion of the first alkylation overhead stream is absorbed into a de-ethanized aromatic lean oil stream containing benzene and alkylbenzene in an absorption zone to produce a rich oil stream containing olefins and at least some of the ethane. The rich oil stream is sent to a second alkylation reaction zone containing a second alkylation catalyst under second alkylation reaction conditions to produce a first aromatic lean oil stream, which is fractionated in a de-ethanizer to produces a de-ethanizer vapor overhead containing a major portion of the ethane and a liquid bottoms containing the de-ethanized aromatic lean oil.

7 Claims, 2 Drawing Sheets

U.S. PATENT DOCUMENTS

| | | |
|---|---|---|
| 4,051,191 A | 9/1977 | Ward |
| 4,083,886 A | 4/1978 | Michalko |
| 4,169,111 A | 9/1979 | Wight |
| 4,215,011 A | 7/1980 | Smith, Jr. |
| 4,232,177 A | 11/1980 | Smith, Jr. |
| 4,242,530 A | 12/1980 | Smith, Jr. |
| 4,250,052 A | 2/1981 | Smith, Jr. |
| 4,302,356 A | 11/1981 | Smith, Jr. |
| 4,307,254 A | 12/1981 | Smith, Jr. |
| 4,316,997 A | 2/1982 | Vaughan |
| 4,371,714 A | 2/1983 | Young |
| 4,423,254 A | 12/1983 | Olah |
| 4,443,559 A | 4/1984 | Smith, Jr. |
| 4,459,426 A | 7/1984 | Inwood et al. |
| 4,469,908 A | 9/1984 | Burress |
| 4,540,831 A | 9/1985 | Briggs |
| 4,570,027 A | 2/1986 | Boucher et al. |
| 4,587,370 A | 5/1986 | DeGraff |
| 4,695,665 A | 9/1987 | DeGraff |
| 4,849,569 A | 7/1989 | Smith, Jr. |
| 4,857,666 A | 8/1989 | Barger et al. |
| 4,870,222 A | 9/1989 | Bakas et al. |
| 4,891,458 A | 1/1990 | Innes et al. |
| 4,922,053 A | 5/1990 | Waguespack et al. |
| 5,003,119 A | 3/1991 | Sardina et al. |
| 5,030,786 A | 7/1991 | Shamshoum et al. |
| 5,118,894 A | 6/1992 | Le |
| 5,177,285 A | 1/1993 | Van Opdorp et al. |
| 5,334,795 A | 8/1994 | Chu et al. |
| 5,336,821 A | 8/1994 | DeGraff et al. |
| 5,602,290 A | 2/1997 | Fallon |
| 5,723,710 A | 3/1998 | Gajda et al. |
| 5,856,607 A | 1/1999 | Kim |
| 5,902,917 A | 5/1999 | Collins et al. |
| 5,977,423 A | 11/1999 | Netzer |
| 5,998,684 A | 12/1999 | Ho et al. |
| 6,002,057 A | 12/1999 | Hendriksen et al. |
| 6,060,632 A | 5/2000 | Takamatsu et al. |
| 6,096,935 A | 8/2000 | Schulz et al. |
| 6,252,126 B1 | 6/2001 | Netzer |
| 6,281,399 B1 * | 8/2001 | Schulz et al. ............... 585/323 |
| 6,376,729 B1 * | 4/2002 | Merrill et al. ............... 585/449 |
| 6,486,371 B1 * | 11/2002 | Butler et al. ................ 585/449 |
| 6,620,387 B1 * | 9/2003 | Sy ............................. 422/194 |
| 6,762,334 B1 * | 7/2004 | Stewart et al. .............. 585/323 |
| 6,995,295 B2 * | 2/2006 | Clark et al. ................. 585/449 |
| 7,074,978 B2 * | 7/2006 | Pohl ........................... 585/449 |
| 2002/0182124 A1 * | 12/2002 | Woodard et al. ............ 422/149 |
| 2003/0028059 A1 * | 2/2003 | Hamper et al. .............. 585/323 |
| 2004/0167371 A1 * | 8/2004 | Pohl ........................... 585/449 |

* cited by examiner

PROCESS FOR THE PRODUCTION OF ALKYLBENZENE WITH ETHANE STRIPPING

CROSS REFERENCE TO RELATED APPLICATIONS

The present application is a divisional of U.S. patent application Ser. No. 10/457,863 filed Jun. 10, 2003, now U.S. Pat. No. 7,071,369 to which priority is claimed.

BACKGROUND

1. Technical Field

The present disclosure relates to an alkylation process for the production of an alkylaromatic from an olefin and an aromatic, and particularly to the production of ethylbenzene from ethylene and benzene.

2. Background of the Art

Various processes for the production of alkylbenzene by the alkylation of benzene with an olefin are known in the art. Among the most common olefins used are ethylene and propylene. The alkylation of benzene with ethylene produces ethylbenzene. The alkylation of benzene with propylene produces cumene.

Ethylbenzene is an important chemical used mostly as a precursor for the production of styrene, which is subsequently polymerized to produce polystyrene. Various methods are known for the production of ethylbenzene. Typically, benzene and ethylene are combined in an alkylation reaction in the presence of a suitable catalyst. Various alkylation catalysts are known, and commonly used catalysts include Friedel-Crafts catalysts such as aluminum or boron halides, and various zeolites.

The reaction produces, in addition to ethylbenzene, a byproduct containing polyethylbenzenes ("PEB") such as diethylbenzene, triethylbenzene and tetraethylbenzene. The polyethylbenzenes are undesirable and are usually recycled to a transalkylation reactor for conversion to ethylbenzene by reaction with benzene.

Ethylbenzene has been produced in a process wherein the alkylation reaction was performed by catalytic distillation. The zeolite catalyst is contained in specially packaged bales, and the alkylation reaction is conducted in mixed vapor-liquid phase.

U.S. Pat. No. 5,003,119 to Sardina et al., which is incorporated by reference herein, discloses a process for the manufacture of alkylbenzenes, such as ethylbenzene and cumene, wherein a feed of fresh and recycle benzene and fresh olefin are reacted in the presence of an alkylation catalyst in an alkylator having at least two reaction stages wherein each stage is adiabatic. Essentially all of the olefin is completely reacted in each stage of the alkylator. Fresh olefin is fed into each stage of the alkylator.

Up to now, for a dilute ethylene feed, 99% of the ethylene conversion has been achieved in the alkylator. This level of conversion requires a large amount of catalyst. The vent gas from the alkylator is sent to a vent absorber where the benzene is absorbed in a hydrocarbon stream (e.g., polyethylbenzenes). The ethylene contained in the vent gas was ultimately lost. It would be advantageous to have a substantially complete conversion of ethylene with a reduced overall amount of required catalyst.

SUMMARY OF THE INVENTION

A process for the production of alkylbenzene is provided herein. The process comprises the steps of (a) introducing benzene and an olefin feed into a first alkylation reaction zone in the presence of a first alkylation catalyst under first alkylation reaction conditions to produce a first alkylation effluent containing alkylbenzene and a first alkylation overhead stream, (b) separating the first alkylation overhead stream into a liquid portion containing benzene and a vapor portion containing unconverted olefin and ethane, (c) absorbing a major portion of the unconverted olefin in the vapor portion of the first alkylation overhead stream into a de-ethanized aromatic substantially olefin-free lean oil stream containing benzene and alkylbenzene in an absorption zone to produce a rich oil stream containing olefins and at least some of the ethane; (d) introducing the rich oil stream into a second alkylation reaction zone containing a second alkylation catalyst under second alkylation reaction conditions to produce a first aromatic lean oil stream; and, (e) fractionating the first aromatic lean oil stream in a de-ethanizer to produces a de-ethanizer vapor overhead containing a major portion of the ethane and a liquid bottoms containing the de-ethanized aromatic lean oil.

The process is particularly suited for the purpose of making ethylbenzene and requires much less catalyst than prior systems while achieving higher overall conversion of ethylene.

BRIEF DESCRIPTION OF THE DRAWINGS

Various embodiments are described herein with reference to the drawings wherein.

DETAILED DESCRIPTION OF PREFERRED EMBODIMENT(S)

The alkylation process of the present invention can be employed for alkylation of benzene with any suitable olefin, such as ethylene, propylene, and the like. However, the process herein is particularly advantageous for the production of ethylbenzene and will be described in connection with the alkylation of benzene with ethylene. It should be remembered that propylene or other olefins may also be used and are considered to be within the scope of the present invention.

The process of the present invention includes a second alkylation finishing reactor to convert substantially all of the remaining olefin carried over in the vent gas from the alkylator. This improvement prevents the loss of olefin yield and reduces the amount of catalyst required in the alkylator. The process herein also includes an ethane stripper for reducing the volume of inerts cycled through the finishing reactor system.

Figure 1:
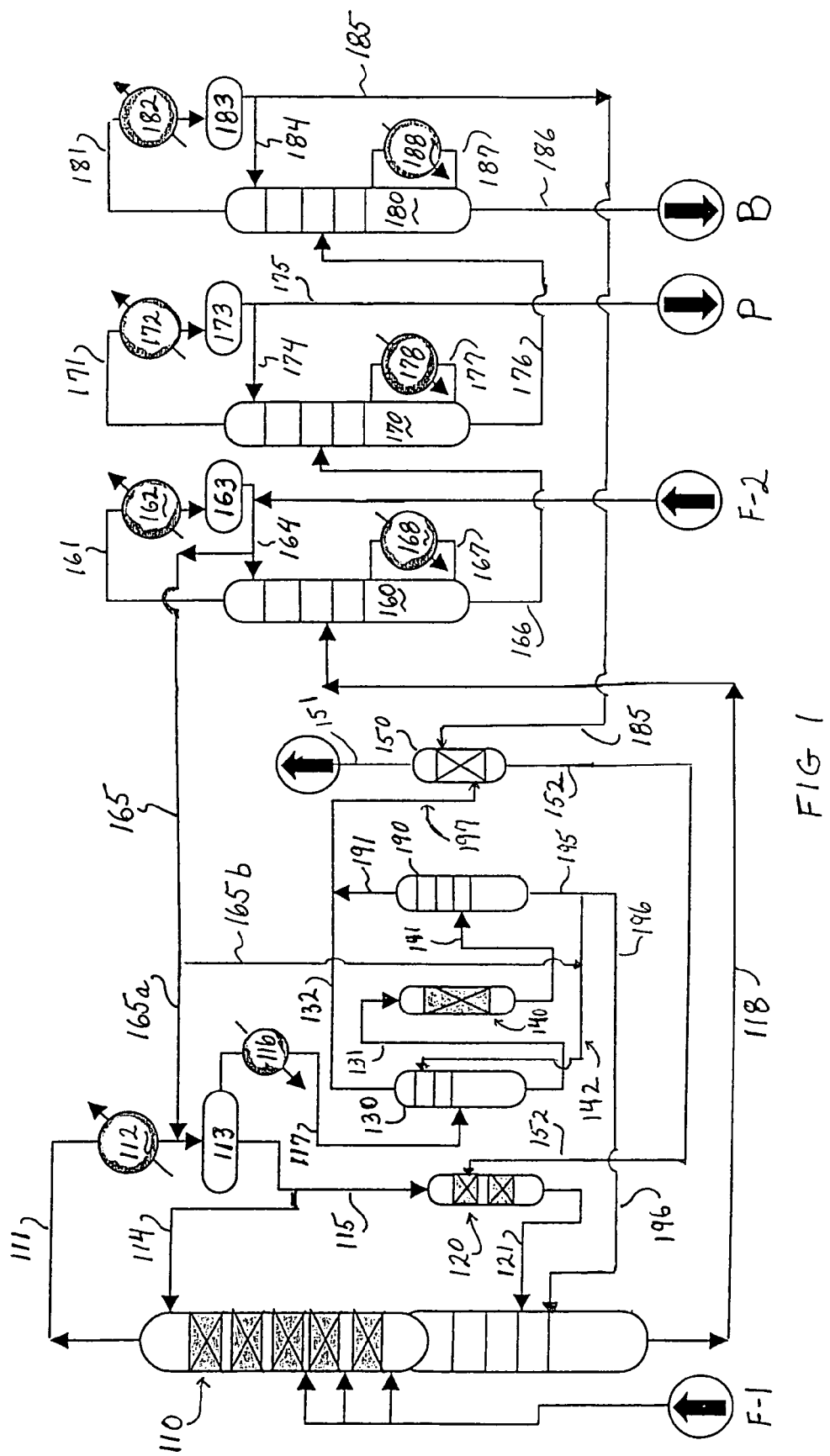
FIG. 1 is schematic flow chart of the process for producing ethylbenzene.

Referring to FIG. 1, an ethylene feed F-1 and a benzene feed F-2 are introduced into the ethylbenzene production process 100 as shown. Ethylene feed F-1 can contain 5% to 100% by volume of ethylene, and can optionally be an offgas from a refinery operation such as FCC, which generally contains about 10% to about 30% by volume of ethylene. A typical FCC offgas contains 50% to 70% methane and hydrogen, with the balance being about equal amounts of ethane and ethylene and minor amounts of other hydrocarbon components. A preferred feedstock F-1 contains 30% to 50% by volume of ethylene with the rest of the components including methane, ethane, hydrogen and other components. Optionally, the feed F-1 to the alkylator 110 can be polymer grade ethylene. Ethylene feed F-1 is sent to an alkylator 110 which is preferably a catalytic distillation column including a suitable alkylation catalyst such as one or more catalyst selected from zeolite X, zeolite Y, zeolite L, TMA Offretite, mordenite, and amorphous silica-alumina, zeolite BEA (beta), zeolite MWW, or MFI catalyst, Zeolite BEA is preferred. The catalyst is optionally contained in packaged bales.

Various types of catalytic distillation apparatus and methods and apparatus are known in the art. Alkylator 110 is mixed phase (liquid/vapor) reactor operating at alkylation reaction conditions, typically at a pressure of from about 270 psig to about 550 psig and a temperature of from about 185° C. to about 250° C., and a phenyl:ethyl ratio ranging from about 2.0 to about 3.5.

Alkylator 110 is suited to handle dilute ethylene feed and is capable of handling variations in the ethylene content and flow rate.

The feed F-1 is preferably injected at multiple points in the reactor and is contacted and dissolved in the liquid benzene introduced into the alkylator 110 via line 114 and flowing downward through the catalyst packing in the column 110. The ethylene absorbed by the benzene reacts with the benzene upon contact with the catalyst to form ethylbenzene and minor amounts of PEB. The outflow of liquid from the bottom of the alkylator 110 (i.e., the ethylbenzene-containing liquid) is sent via line 118 to distillation column 160. Column 160 separates benzene from the ethylbenzene product and heavier components. The benzene is distilled overhead as a vapor and is sent via line 161 to condenser 162 where it is liquified and held in accumulator 163. Benzene from accumulator 163 is sent via line 164 back to column 160 as a reflux. A portion 165 of the benzene is drawn off from line 164 and is sent via line 165*a* to the overhead from the alkylator 110, and via line 165*b* to the vent absorber 130 as described more fully below. Fresh benzene feed F-2 is preferably introduced into line 164.

Alternatively, the fresh benzene can be fed to other places in the process that are benzene rich. The fresh benzene should be free of amines, aldehydes, ketones, and basic nitrogen compounds, which can poison the catalysts used in the process. Bottom stream 167 is recirculated back to the column 160 through reboiler 168.

A bottom stream 166 containing ethylbenzene and PEB is sent to distillation column 170. Column 170 separates the ethylbenzene product from PEB. Bottom stream 177 is recirculated back to ethylbenzene column 170 through reboiler 178. Bottom stream 176 containing PEB is sent to distillation column 180 for separation of PEB. The overhead ethylbenzene vapor stream 171 from column 170 is liquified in condenser 172 and sent to accumulator 173. A portion of the overhead is returned to column 170 as reflux via line 174. Another portion is withdrawn via line 175 as ethylbenzene product P.

Column 180 separates the PEB (e.g., diethyl benzene) from a heavy flux oil. The bottom stream 187 is recirculated back to column 180 through reboiler 188. A portion of the bottoms is withdrawn via line 186 as a heavy flux oil B. Flux oil typically contains diphenylethane, tetraethylbenzene, and other high boiling components, and can be used as a heat transfer fluid, fuel oil or an absorbent. The overhead PEB vapor stream 181 is liquified in condenser 182 and sent to accumulator 183. A portion of the overhead is returned to column 180 via line 184 as a reflux. Another portion of the PEB overhead is sent via line 185 to vent stripper 150, as explained in further detail below.

Considering once again the alkylator 110, the overhead vapor 111 from the alkylator contains unconverted olefin as well as ethane and one or more light components such as hydrogen, methane, carbon monoxide, carbon dioxide, propane and/or nitrogen, and is partially liquified by condenser 112 and sent to accumulator 113. Also received into the accumulator 113 is a portion 165*a* of the benzene stream 165, which is divided into portions 165*a* and 165*b*. Accordingly, accumulator 113 contains combined recycled benzene and condensed alkylator overhead as well as uncondensed vapor. A portion of the liquid from accumulator 113 is sent back to the alkylator 110 as a reflux. Another portion is sent via line 115 to transalkylator 120. Transalkylator 120 also receives a stream of PEB from vent stripper 150 via line 152. In the transalkylator 120 the benzene (from line 115) and the PEB (from line 152) react to form ethylbenzene, which is recycled back to alkylator 110 via line 121.

Transalkylator 120 contains a suitable transalkylation catalyst such as zeolite beta, zeolite Y or other suitable zeolite, and is operated under suitable transalkylation reaction conditions. Typically, transalkylation reaction conditions include a temperature of from 185° C. to about 250° C., a pressure of from about 350 psig to about 600 psig, a space velocity of from about 3.5 to 5.0 WHSV, and a molar ratio of phenyl to ethyl of from about 2.0 to about 5.0, wherein 3.0 is preferred.

The uncondensed vapor from accumulator drum 113 is heated in heat exchanger 116 and the vapor stream containing ethylene, benzene and inerts such as ethane, methane and hydrogen is sent via line 117 to vent absorber 130 for recovery of aromatics.

Figure 2:
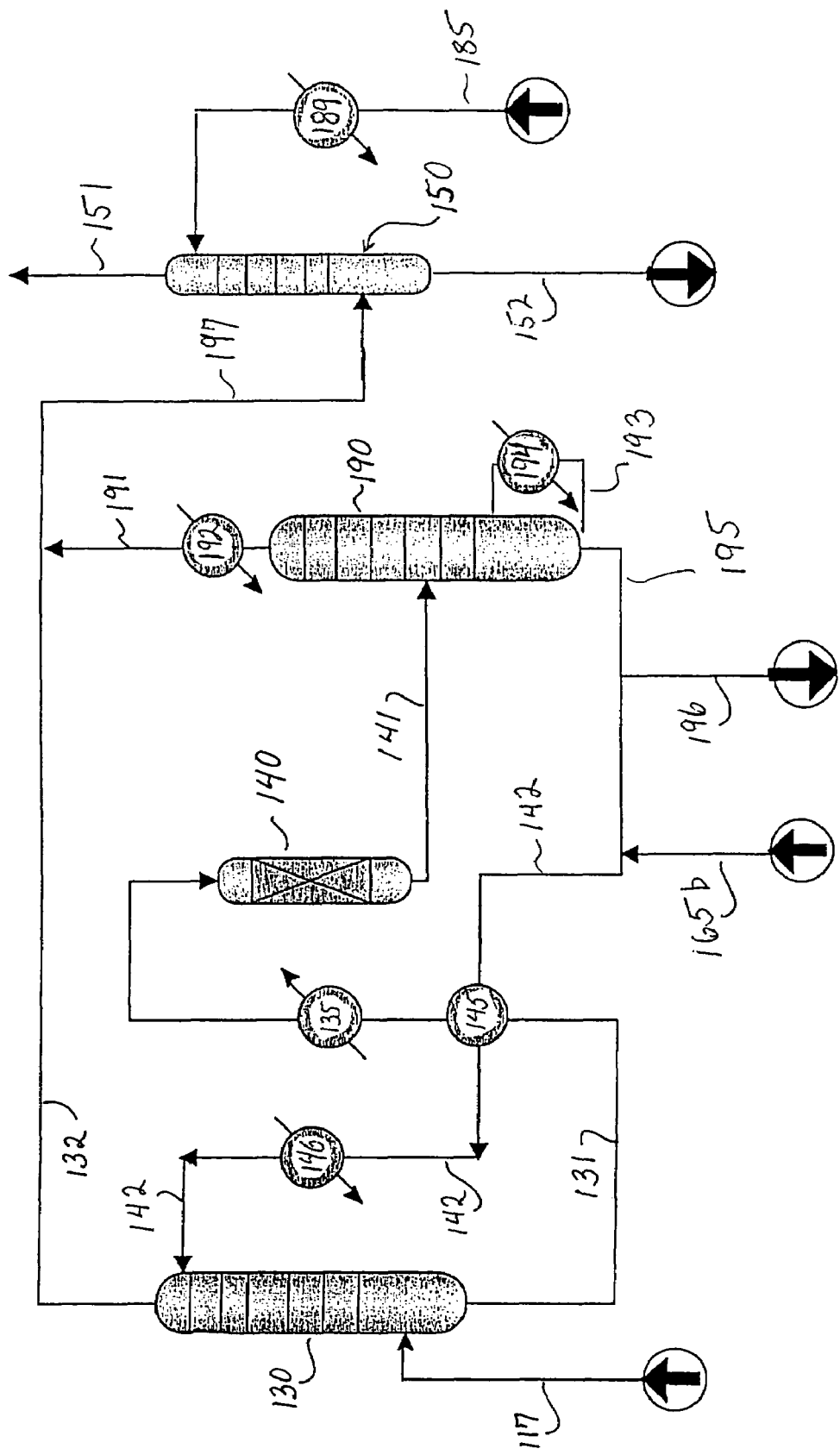
FIG. 2 is a more detailed view of a portion of the process.

Referring now to both FIG. 1 and FIG. 2, the vapor stream flowing upward in vent absorber 130 is contacted with a downward flow of de-ethanized substantially olefin-free lean oil from line 142 containing benzene and ethylbenzene but substantially no ethylene. Vent absorber 130 can be a packed column or a tray column operating in countercurrent mode. Vent absorber columns are known in the art.

The de-ethanized lean oil dissolves almost all of the ethylene. The loss of ethylene in the overhead vapor (line 132) from the vent absorber 130 is about 1.0% of the ethylene fed to the unit (line 117). The bottoms from the vent absorber 130 containing a rich oil (i.e., with dissolved-ethylene) is sent via line 131 to a finishing reactor 140 for conversion of ethylene and benzene to ethylbenzene. The rich oil stream contains at least 0.2% by weight of ethylene, preferably at least about 0.3 wt % ethylene, and more preferably at least about 0.4 wt % ethylene, and at least about 5.0 wt % ethylbenzene, preferably at least about 10 wt % ethylbenzene, and more preferably at least about 13 wt % ethylbenzene. The rich oil stream first passes through heat exchanger 145 wherein heat is transferred from the de-ethanized lean oil (line 142) from the finishing reactor 140 to the rich oil stream in line 131. The rich oil stream is further heated in heater 135 and sent to the finishing reactor 140.

Finishing reactor 140 is a second alkylator which contains a fixed bed of loose catalyst, preferably zeolite Y or, zeolite BEA (beta), zeolite MWW, Mordenite, or MFI catalyst and operates adiabatically in a single, liquid phase. Alkylation in the liquid phase is more efficient and requires less catalyst than alkylation in the mixed vapor/liquid phases. Conversion of ethylene in this reactor 140 is substantially complete. Finishing reactor 140 operates at a temperature of from about 200° C. to about 230° C., a pressure of from about 550 psig to about 900 psig, and a phenyl:ethyl mole ratio of from about 2.0 to about 10.0. The high phenyl:ethyl mole ratio results in excellent catalyst selectivity and stability.

The effluent stream 141 from the finishing reactor carries a lean oil containing benzene and ethylbenzene along with dissolved ethane and methane.

This lean oil is sent to de-ethanizer 190, which removes inert light components such as ethane and methane. The de-ethanizer is a distillation column for removing light components. The overhead 191 from the de-ethanizer is first sent through condenser 192, with the liquified portion being refluxed to the de-ethanizer column 190. The remaining vapor is added to stream 132 (the overhead from the vent absorber 130) to form stream 197, which is then sent to the vent gas scrubber 150. Overhead 191 contains ethane, methane, traces of water, non-aromatics and benzene. Optionally, overhead 191 can alternatively be sent to a cracking furnace for re-use of the ethane. Bottom stream 193 of the de-ethanizer is cycled through reboiler 194 and re-introduced into de-ethanizer column 190. Another portion 195 is drawn off the bottom of the de-ethanizer. The bottom effluent 195 from the de-ethanizer carrier a de-ethanized lean oil containing benzene and ethylbenzene. A portion 196 of the de-ethanizer bottoms is cycled back to the alkylator 110 via line 196 to maintain the liquid inventory in the absorber system, and carries the net amount of ethylbenzene made in finishing reactor 140.

A portion 165*b* of the benzene from the overhead 165 of the benzene column is fed into the lean oil stream to maintain a desired benzene concentration in the stream, which provides the desired selectivity in the finishing reactor 140. The resulting stream 142 is cooled against the effluent 131 from the vent absorber in heat exchanger 145, as stated above, and is further chilled in cooler 146 to a temperature ranging from about 6° C. to about 40° C., preferably is 12°, whereupon it is fed to the top of the vent absorber 130.

The overhead vapor from the vent absorber 130 containing methane, ethane, hydrogen, traces of water, non-aromatics, benzene and ethylene, is carried by stream 132. As stated above, the overhead 191 from the de-ethanizer is added to overhead stream 132 from the vent absorber to form stream 197, which is introduced to the vent scrubber 150 for aromatic recovery where the upflow of vent gas is contacted with downflow of PEB from the PEB column 180. The vent scrubber 150 is operated to reject into the overhead gas (line 151) a small amount of $C_6$ non-aromatics and benzene as well as the inerts (hydrogen, methane, ethane, water, etc). The PEB stream 185 from column 180 is first chilled in a cooler 189 and then introduced at the top of the vent scrubber column 150. The scrubbed vent gas exits the vent scrubber 150 via line 151. Very little ethylene is vented from the vent scrubber 150. The overall ethylene conversion of the process is about 99.9%. The bottoms from the vent scrubber 150 containing PEB and other aromatics are sent to the transalkylator 120 via line 152 for conversion of the PEB to ethylbenzene by transalkylation with benzene.

By using a de-ethanizer column to remove light components (ethane, methane) from the lean oil, less burden is put upon the finishing reactor to accommodate the unnecessary throughput of the inert components.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A system for the production of alkylbenzene comprising:
   a) first alkylator means for alkylating benzene with an olefin, wherein the first alkylator means produces an effluent containing alkylbenzene and benzene, and an overhead stream;
   b) condensing means for separating the overhead stream from the first alkylator means into a vapor stream and a liquid stream;
   c) transalkylator means for contacting the liquid stream from the first alkylator means overhead with a stream containing polyalkylbenzene to produce a transalkylator effluent containing alkylbenzene and benzene;
   d) absorber means for contacting the vapor stream from the first alkylator means overhead with a de-ethanized lean oil stream containing benzene and alkylbenzene to produce a rich oil stream containing benzene, alkylbenzene and unconverted olefin;
   e) second alkylator means for converting the unconverted olefin and at least some of the benzene in the rich oil stream to produce a first lean oil stream; and,
   f) a fractionator for de-ethanizing the first lean oil stream to produce the de-ethanized lean oil stream.

2. The system of claim 1 wherein the first alkylator means comprises a catalytic distillation unit.

3. The system of claim 1 wherein the absorber means comprises a packed column.

4. The system of claim 1 wherein the absorber means comprises a tray column.

5. The system of claim 1 further comprising a scrubber unit for contacting a vapor overhead from the absorber means with a downflow stream containing polyalkylbenzene.

6. The system of claim 1 further comprising distillation means for separating out benzene and alkylbenzene from the alkylator means effluent.

7. The system of claim 1 further comprising heat transfer means for transferring heat between the de-ethanized lean oil stream and the rich oil stream.

* * * * *